US009587936B2

United States Patent
Yuditsky et al.

(10) Patent No.: US 9,587,936 B2
(45) Date of Patent: Mar. 7, 2017

(54) SCANNING INSPECTION SYSTEM WITH ANGULAR CORRECTION

(71) Applicant: KLA-Tencor Corporation, Milpitas, CA (US)

(72) Inventors: Yury Yuditsky, Mountain View, CA (US); Alexander Slobodov, San Jose, CA (US); Anatoly Romanovsky, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 961 days.

(21) Appl. No.: 13/826,790

(22) Filed: Mar. 14, 2013

(65) Prior Publication Data

US 2014/0278188 A1    Sep. 18, 2014

(51) Int. Cl.
*G01B 21/04* (2006.01)
*G01N 21/95* (2006.01)
*G03F 1/84* (2012.01)

(52) U.S. Cl.
CPC ....... *G01B 21/045* (2013.01); *G01N 21/9501* (2013.01); *G03F 1/84* (2013.01)

(58) Field of Classification Search
CPC ............. G01B 21/045; G01N 21/9501; G01N 2201/10; G01N 2201/104; G03F 1/84; H01L 21/67288
USPC ....... 356/138, 139, 140, 141, 142, 143, 144, 356/145, 146, 147, 148, 149, 150, 151, 356/152, 152.3, 139.04, 231, 239.8, 356/237.3, 237.4, 614, 615, 622, 141.5; 702/85, 104, 151; 255/559.37, 231.18; 269/57, 58, 63
See application file for complete search history.

(56) References Cited

U.S. PATENT DOCUMENTS

| | | | |
|---|---|---|---|
| 7,397,554 B1 * | 7/2008 | Li | H01L 21/67294 356/237.1 |
| 2005/0105791 A1 * | 5/2005 | Lee | G01N 21/47 382/145 |
| 2009/0225399 A1 * | 9/2009 | Zhao | G01N 21/8806 359/298 |

* cited by examiner

*Primary Examiner* — Gregory J Toatley
*Assistant Examiner* — Kyle R Quigley
(74) *Attorney, Agent, or Firm* — Spano Law Group; Joseph S. Spano (57) ABSTRACT

A wafer is moved under an inspection spot by a rotary inspection system. The system rotates the wafer about an axis of rotation and translates the wafer along a linear trajectory. When the inspection spot is not aligned with the trajectory of the axis of rotation, an angular error is introduced in the representation of the position of the inspection spot with respect to the wafer by the rotary encoder. The angular error is corrected based on an angular error correction value. The angular error correction value is determined based on the distance between the inspection spot and the trajectory of the axis of rotation, the radial distance between the axis of rotation and the inspection spot at a first instance of a particular angular position, and a second radial distance between the axis of rotation and the inspection location at a second instance of the angular position.

21 Claims, 6 Drawing Sheets

FIG. 7

SCANNING INSPECTION SYSTEM WITH ANGULAR CORRECTION

TECHNICAL FIELD

The described embodiments relate to optical metrology and inspection systems operated in a rotary scanning mode, and more particularly to methods and systems for improved imaging performance.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

One such inspection system is a multi-spot wafer inspection system that illuminates and inspects a number of different areas of a wafer surface, simultaneously. Improvements to multi-spot inspection systems are desired to correctly identify the location of an inspection spot with respect to the wafer surface to improve imaging performance of a given tool and over multiple tools.

SUMMARY

A rotary inspection system employs a rotary stage to rotate a wafer about an axis of rotation and a translation stage to translate the wafer along a linear trajectory of the axis of rotation. The rotary inspection system coordinates the motion of the rotary stage and the translation stage to scan the surface of the wafer under a fixed inspection spot. Typically, the angular position of the wafer under the inspection spot is determined by a rotary encoder attached to the rotary stage. When the inspection spot is not aligned with the trajectory of the axis of rotation, an angular error is introduced in the representation of the position of the inspection spot with respect to the wafer by the rotary encoder. Since, traditionally, data acquisition is triggered by an interpolation of encoder pulses generated by the rotary encoder, the error results in data being mapped to an incorrect location on the wafer surface.

In one aspect, the angular error is corrected based on an angular error correction value. The angular error correction value is determined based on the distance between the inspection spot and the trajectory of the axis of rotation, the radial distance between the axis of rotation and the inspection spot at a first instance of a particular angular position, and a second radial distance between the axis of rotation and the inspection location at a second instance of the angular position.

In some examples, the error in the representation of the position of the inspection spot with respect to the wafer by the rotary inspection system is corrected by shifting the timing of data acquisition on the fly to collect data at the correct location on the wafer.

In some other examples, the angular correction is applied as a post-processing step. In some embodiments, the data has already been collected based on uncorrected trigger points. The angular error can be removed from each sample by remapping each sample to a corrected set of polar coordinates in the wafer coordinate frame. This can be achieved using an angular correction value computed for each sample point.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
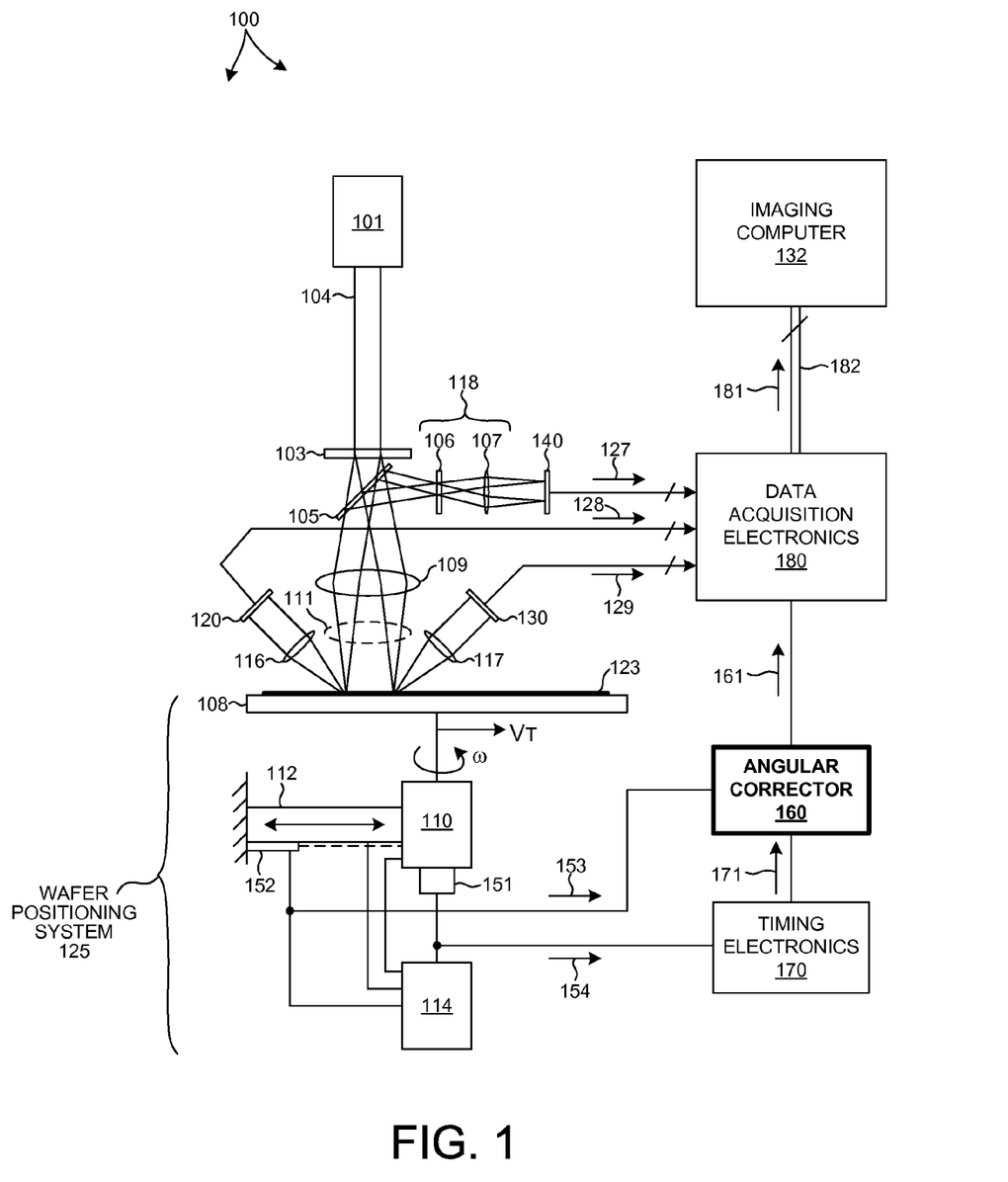
FIG. 1 is a simplified schematic view of a multi-spot inspection system 100 configured to perform angular correction as described herein.

FIG. 1 is a simplified schematic view of one embodiment of a multi-spot inspection system 100 that may be used to perform the angular correction methods described herein. For simplification, some optical components of the system have been omitted. By way of example, folding mirrors, polarizers, beam forming optics, additional light sources, additional collectors, and detectors may also be included. All such variations are within the scope of the invention described herein. The inspection system described herein may be used for inspecting patterned, as well as unpatterned wafers.

As illustrated in FIG. 1, a wafer 123 is illuminated by a normal incidence beam 104 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

Figure 4:
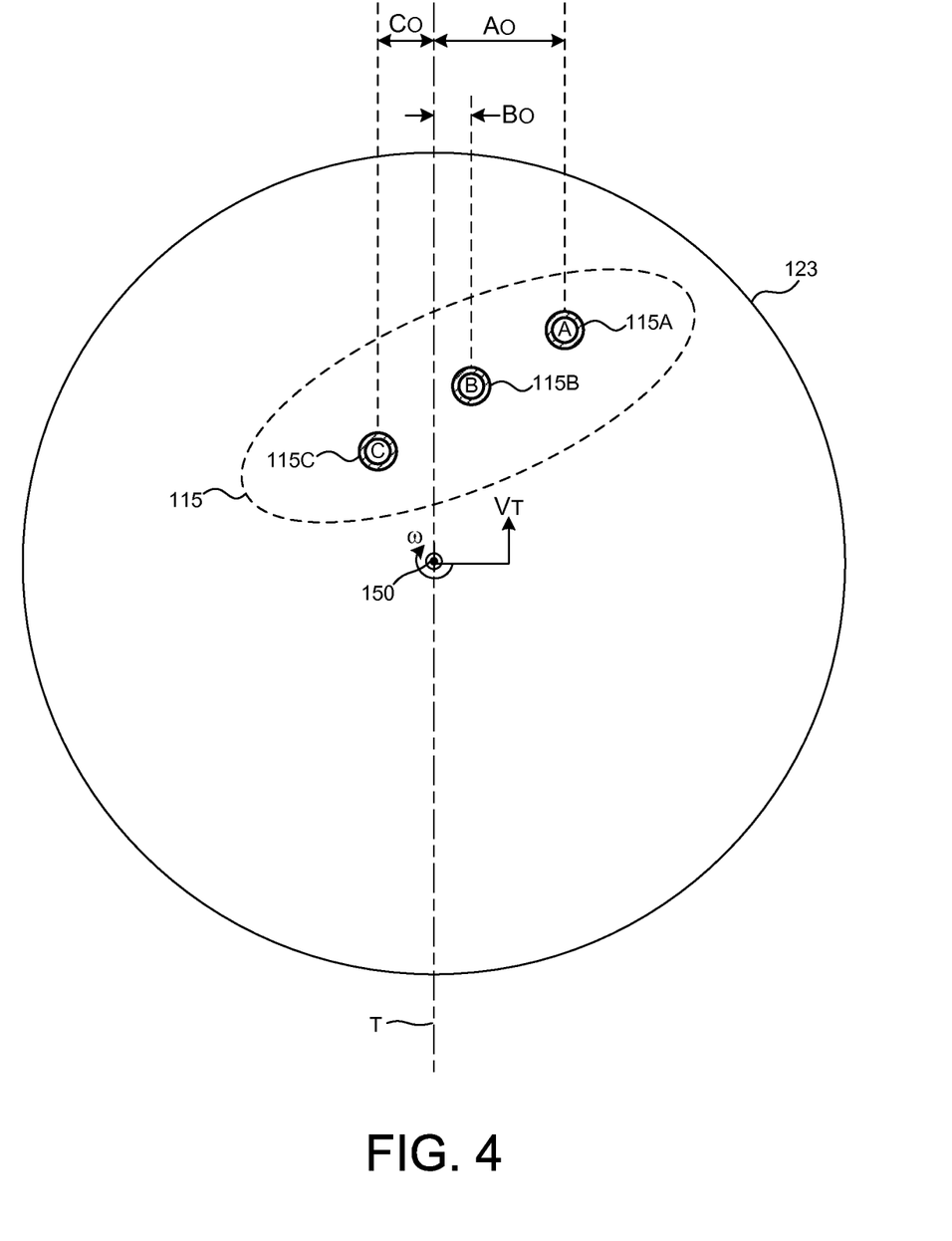
FIG. 4 is a diagram illustrative of an array of incident spots 115 on wafer 123.

System 100 includes a spot array generator 103 that generates a desired beamlet array 111 from the output of illumination source 101. This "generated beamlet array" is directed to the wafer surface. To eliminate confusion, the light that reaches the surface of the wafer is referred to herein as the "incident beamlet array" or the "incident spot array" (e.g., incident spot array 115 illustrated in FIG. 4). As illustrated in FIG. 4, the incident spot array 115 includes incident spots 115A, 115B, and 115C. The incident spots are inspection spots on the surface of wafer 123. The "incident spot array" may differ from the "generated beamlet array" in one or more ways, including polarization, intensity, size and shape of the spot, etc. In one embodiment, spot array generator 103 includes a diffractive optical element to generate the desired number of spots, size of each spot, and spacing between spots. The size, number, and spacing between spots may be determined by a user or may be automatically generated by system 100. A beam splitter 105 directs the beamlet array to an objective lens 109. Objective lens 109 focuses the beamlet array 111 onto a wafer 123 to form incident spot array 115. In this manner, incident spot array 115 is defined (i.e., shaped and sized) by the projection of light emitted from spot array generator 103 onto the surface of wafer 123.

System 100 includes collection optics 116, 117, and 118 to collect the light scattered and/or reflected by wafer 123 during the scan and focus that light onto detector arrays 120, 130, and 140, respectively. The outputs of detectors 120, 130, and 140 are supplied to data acquisition electronics 180. Data acquisition electronics 180 includes an analog-to-digital converter (ADC) to convert the amplified signals into a digital format suitable for use within computer 132. Data acquisition electronics 180 periodically samples the outputs of detectors 120, 130, and 140, and transmits the sampled data 181 to an imaging computer 132 over a fiber channel 182. In one embodiment, a processor of computer 132 may be coupled directly to an ADC by a transmission medium (e.g., fiber channel 182). Alternatively, the processor may receive signals from other electronic components coupled to the ADC. In this manner, the processor may be indirectly coupled to the ADC by a transmission medium and any intervening electronic components.

Imaging computer 132 processes the signals and determines the presence of anomalies and their characteristics. An image of the scanned area can be obtained by re-arranging the outputs from the plurality of channels (e.g., from each of detector arrays 120, 130, and 140), which have been stored in a memory (e.g., a memory of imaging computer 132).

Any of collection optics 116-118 may be a lens, a compound lens, or any appropriate lens known in the art. Alternatively, any of collection optics 116-118 may be a reflective or partially reflective optical component, such as a mirror. In addition, although particular collection angles are illustrated in FIG. 1, it is to be understood that the collection optics may be arranged at any appropriate collection angle. The collection angle may vary depending upon, for example, the angle of incidence and/or topographical characteristics of the specimen.

Each of detectors 120, 130, and 140 generally function to convert the scattered light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen. The term "single detector" is used herein to describe a detector having only one sensing area, or possibly several sensing areas (e.g., a detector array or multi-anode PMT). Regardless of number, the sensing areas of a single detector are embodied within a single enclosure.

System 100 also includes various electronic components (not shown) needed for processing the scattered signals detected by any of detectors 120, 130, and 140. For example, system 100 may include amplifier circuitry to receive output signals from any of detectors 120, 130, and 140 and to amplify those output signals by a predetermined amount.

In general, a processor of imaging computer 132 is configured to detect features, defects, or light scattering properties of the wafer using electrical signals obtained from each detector. The signals produced by the detector are representative of the light detected by a single detector (e.g., detector 120, detector 130, or detector 140). The processor may include any appropriate processor known in the art. In addition, the processor may be configured to use any appropriate defect detection algorithm or method known in the art. For example, the processor may use a die-to-database comparison or a thresholding algorithm to detect defects on the specimen.

In addition, multi-spot inspection system 100 may include peripheral devices useful to accept inputs from an operator (e.g., keyboard, mouse, touchscreen, etc.) and display outputs to the operator (e.g., display monitor).

System 100 can use various imaging modes, such as bright field, dark field, and confocal. For example, in one embodiment, detector array 140 generates a bright field image. As illustrated in FIG. 1, some amount of light scattered from the surface of wafer 123 at a narrow angle is collected by objective lens 109. This light passes back through objective lens 109 and impinges on beam splitter 105. Beam splitter 105 transmits a portion of the light to collection optics 118, which in turn focuses the light onto detector array 140. In this manner a bright field image is generated by detector array 140. Collection optics 118 include imaging lens 107 that images the reflected light collected by objective lens 109 onto detector array 140. An aperture or Fourier filter 106, which can rotate in synchronism with the wafer, is placed at the back focal plane of objective lens 109. Various imaging modes such as bright field, dark field, and phase contrast can be implemented by using different apertures or Fourier filters. U.S. Pat. Nos. 7,295,303 and 7,130,039, which are incorporated by reference herein, describe these imaging modes in further detail. In another example, detector arrays 120 and 130 generate dark field images by imaging scattered light collected at larger field angles. In another example, a pinhole array that matches the layout of the illumination spot array can be placed in front of each detector array 120, 130, and 140 to generate a confocal image. U.S. Pat. No. 6,208,411, which is incorporated by reference herein, describes these imaging modes in further detail. In addition, various aspects of surface inspection system 100 are described in U.S. Pat. No. 6,271,916 and U.S. Pat. No. 6,201,601, both of which are incorporated herein by reference.

In the embodiment illustrated in FIG. 1, wafer positioning system 125 moves wafer 123 under a stationary beamlet array 111. Wafer positioning system 125 includes a wafer chuck 108, motion controller 114, a rotation stage 110 and a translation stage 112. Wafer 123 is supported on wafer chuck 108. Wafer 123 is located with its geometric center approximately aligned the axis of rotation of rotation stage 110. In this manner, rotation stage 110 spins wafer 123 about its geometric center at a specified angular velocity, $\omega$, within an acceptable tolerance. In addition, translation stage 112 translates the wafer 123 in a direction approximately perpendicular to the axis of rotation of rotation stage 110 at a specified velocity, $V_T$. Motion controller 114 coordinates the spinning of wafer 123 by rotation stage 110 and the translation of wafer 123 by translation stage 112 to achieve the desired spiral scanning motion of wafer 123 within multi-spot inspection system 100. As such, inspection system 100 is a rotary inspection system.

Figure 2:
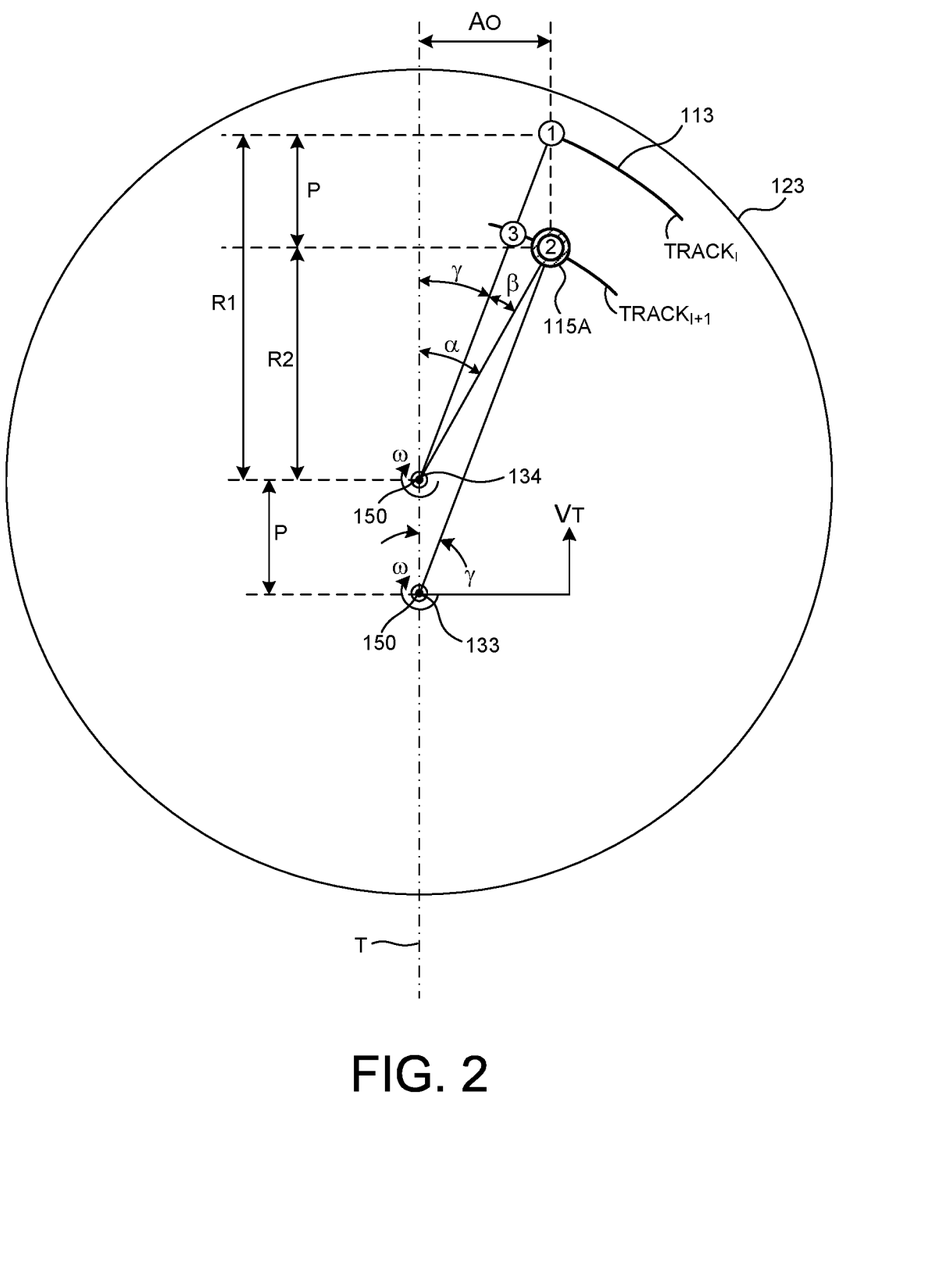
FIG. 2 is a diagram illustrative of a wafer 123 undergoing inspection in a rotary inspection system with an incident spot 115A that is not aligned with the trajectory of the axis of rotation.

In an exemplary operational scenario, inspection begins with incident spot array 115 located at the outer perimeter of wafer 123 and wafer 123 is rotated and translated until incident spot array 115 reaches the center of wafer 123. Due to the coordinated motion of rotation stage 110 and translation stage 112, the locus of points illuminated by incident spot array 115 traces a spiral path on the surface of wafer 123. The spiral path on the surface of wafer 123 is referred to as an inspection track 113 (not shown in its entirety in FIG. 2). Portions of an exemplary inspection track 113 are illustrated in FIG. 2 as $TRACK_i$ and $TRACK_{i+1}$, respectively. The distance between adjacent portions of an inspection track (e.g., distance between $TRACK_{i+1}$ and $TRACK_i$) is referred to as the scan pitch, P, of the multi-spot inspection system 100. Incident spot array 115 may be configured with considerable spacing between beamlets such that inspection results are interleaved among successive portions of a track 113 and cross-talk at the detectors is minimized. U.S. Pat. Publication No. 2009/0225399, which is incorporated by reference herein, describes multi-spot scanning techniques in further detail.

In some embodiments, system 100 may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

Traditionally, each data acquisition sample captured by data acquisition electronics 180 is synchronized with the angular position of wafer 123 fixedly attached to wafer positioning system 125. As illustrated in FIG. 1, rotary stage 110 includes a rotary encoder 151 that generates an output signal 154 (e.g., encoder pulses) indicative of the angular position of wafer 123. Similarly, translation stage 112 includes a linear encoder 152 that generates and output signal 153 indicative of the radial position of wafer 123. Signal 154 is communicated to timing electronics 170. Timing electronics 170 interpolates output signal 154 generated by rotary encoder 151 to generate a signal 171 of high resolution pulses indicative of the angular position of wafer 123. Signal 171 is generated in such way the number of pulses per revolution, or track, is constant. Traditionally, signal 171 was communicated to data electronics 180 to trigger the acquisition of data collected by detectors 120, 130, and 140. In this manner, data collection in a rotary inspection system such as multi-spot inspection system 100 is synchronized with the angular position of wafer 123. Signal 171 is sometimes referred to as an "equiangular clock," and data acquisition is synchronized with the equiangular clock. As such, signal 171 is an uncorrected data acquisition trigger signal.

FIG. 2 is a diagram illustrative of a wafer 123 undergoing inspection in a rotary inspection system with an incident spot 115A that is not aligned with the trajectory of the axis of rotation. A single incident spot 115A is depicted for illustrative purposes. It is important to note that incident spot 115A is an inspection spot fixed to the inspection system 100, while wafer 123 is scanned beneath incident spot 115A. As depicted, wafer positioning system 125 moves wafer 123 radially, along the trajectory of the axis of rotation, T. At the same time, wafer positioning system 125 rotates wafer 123 about the axis of rotation 150. As illustrated in FIG. 2, incident spot 115A is misaligned with trajectory, T, by a distance, $A_O$. This misalignment creates an error in the representation of the position of the incident spot 115A with respect to the wafer by rotary encoder 151. Since, traditionally, data acquisition is triggered by an interpolation of encoder pulses generated by rotary encoder 151, the error results in collected data being mapped to an incorrect location on the wafer surface. In other words, the assumed location on the wafer surface associated with a particular set of sampled data is actually different than the actual location on the wafer surface where the data was collected.

FIG. 2 illustrates two instances of the same angular position, $\gamma$, as measured by rotary encoder 151. A first instance of angular position, $\gamma$, occurs when the axis of rotation 150 of wafer 123 (the same as the axis of rotation of the rotary stage 110) is located at location 133. At this point in time, data acquisition occurs, and data is collected at incident spot 115A. A second instance of angular position, $\gamma$, occurs when the axis of rotation 150 of wafer 123 is located at location 134. For example, wafer 123 rotates one complete revolution to the next instance of angular position, $\gamma$, while it translates along trajectory, T, over a distance, P (the scan pitch). In general, the second instance can be any integer multiple of 360 degrees from the first instance. FIG. 2 illustrates location 1 as the location on wafer 123 where data was collected at the previous instance of angular position, $\gamma$. In other words, location 1 was under incident spot 115A at the previous instance of angular position, $\gamma$. At the second instance of angular position, $\gamma$, the error introduced by the misalignment of incident spot 115A with the trajectory of the axis of rotation, T, becomes clear. From the point of view of wafer 123, the next instance of angular position, γ, should be location 3. However, due to the misalignment of incident spot 115A with the trajectory of the axis of rotation, T, incident spot 115A is over location 2 at the second instance of angular position, γ. In a traditional rotary inspection system, data collection would be triggered at this point in time and associated with location 3, when in fact the data collected should be associated with location 2.

As illustrated in FIG. 2, the misalignment between incident spot 115A and the trajectory of the axis of rotation, T, creates an error in the representation of the position of the incident spot 115A with respect to the wafer by rotary encoder 151. To generate an accurate image of the wafer based on collected data, the data must be associated with the location on the wafer where the data was physically collected.

In summary, data collected by a sensor fixed to the frame of a rotary inspection system must be assigned the correct location in a coordinate frame fixed to the wafer (e.g., a polar coordinate frame fixed to the wafer). When the sensor location is aligned with the translation axis, this assignment is trivial. The angular encoder of the rotary stage provides a direct, accurate representation of the angular position of the sensor relative to a coordinate frame fixed to the wafer (e.g., a polar coordinate frame fixed to the wafer at a location on the wafer that corresponds to the axis of rotation of the rotary stage). Similarly, the translation encoder provides a direct, accurate representation of the radial position of the sensor relative to the coordinate frame fixed to the wafer. However, when there is misalignment of the sensor from the translation axis, the angular encoder, in particular, does not provide a sufficiently accurate representation of the angular position of the sensor relative to a coordinate frame fixed to the wafer. Images generated from collected data associated with locations on the wafer coordinate frame based directly on the angular position measured by the rotary encoder are inaccurate. For example, in many cases, a defect is identified by finding a scattered light signal on two or more tracks with the same angle on the wafer surface. If data is not acquired, or not correctly associated with the same angle on multiple tracks, defect detection may fail. This problem is magnified as the misalignment grows larger, and is a particular problem for multi-spot inspection systems employing a rotary scanning stage, as it is not always practical or desirable to align every inspection spot with the translation axis.

In one aspect, the error in the representation of the position of an inspection spot with respect to the wafer by a rotary inspection system is corrected to compensate for misalignment of the inspection spot with the linear trajectory of the axis of rotation of the wafer.

As illustrated in FIG. 2, the angle, β, is the angular correction between the desired angular position on wafer 123 (location 3) where data should be sampled and the actual position (location 2) on wafer 123 where data would be sampled without correction. Angular correction, β, is calculated and applied to every angular sample coming from rotation encoder to the data acquisition electronics.

As illustrated in FIG. 2, the distance between the trajectory of the axis of rotation, T, and location 1 is $A_O$. The first instance of angular position, γ, is associated with a radial distance, R1, between the axis of rotation 150 of wafer 123 and location 1. Hence the angular offset from the trajectory of the axis of rotation, T, of incident spot 115A in the first instance is:

$$\gamma = ATAN\left(\frac{A_O}{R1}\right) \tag{1}$$

The second instance of angular position, γ, is associated with a radial distance, R2, between the axis of rotation 150 of wafer 123 and location 2. Hence the angular offset from the trajectory of the axis of rotation, T, of incident spot 115A in the second instance is:

$$\alpha = ATAN\left(\frac{A_O}{R2}\right) \tag{2}$$

Thus, when the wafer positioning system 125 makes one complete revolution, incident spot 115A has not yet reached a location on the wafer 123 (location 3) that is at the same angular orientation from the perspective of the wafer. The angular difference is:

$$\beta = \alpha - \gamma = ATAN\left(\frac{A_O}{R2}\right) - ATAN\left(\frac{A_O}{R1}\right) \tag{3}$$

Based on known trigonometric identities, Equation (3) can be rewritten as:

$$\beta = ATAN\left(\frac{A_O(R1 - R2)}{R2 * R1 + A_O^2}\right) \tag{4}$$

For small angles, β can be approximated as:

$$\beta = \frac{A_O(R1 - R2)}{R2 * R1 + A_O^2} \tag{5}$$

In the example depicted in FIG. 2, β, is a positive number, but in other examples, it could be negative number. For example, if incident spot 115A were located on the opposite side of the trajectory of the axis of rotation, T, $A_O$, would be negative. If the rotary stage were to rotate in the opposite direction, γ would be larger than α). If the translation stage were to translate in the opposite direction, R2 would be greater than R1.

A positive β value indicates that the corrected angular sample is delayed relative to the angular sample generated by rotary encoder 151 at the location of incident spot 115A. Similarly, the corrected sampling frequency is lower than the sampling frequency generated by the rotary encoder 151. A negative β value indicates that the corrected angular sample is ahead of the angular sample generated by rotary encoder 151 at the location of incident spot 115A. Similarly, the corrected sampling frequency is higher than the sampling frequency generated by rotary encoder 151.

In some embodiments, the error in the representation of the position of an incident spot with respect to the wafer by a rotary inspection system is corrected by shifting the timing of data acquisition on the fly to collect data at the correct location on the wafer. By way of non-limiting example, multi-spot inspection system 100 includes an angular corrector 160 that receives signal 171 indicative of interpolated encoder pulses from the wafer positioning system and communicates a corrected trigger signal 161 to data acquisition electronics 180 such that the data collected is associated with the correct location on the wafer.

Figure 3:
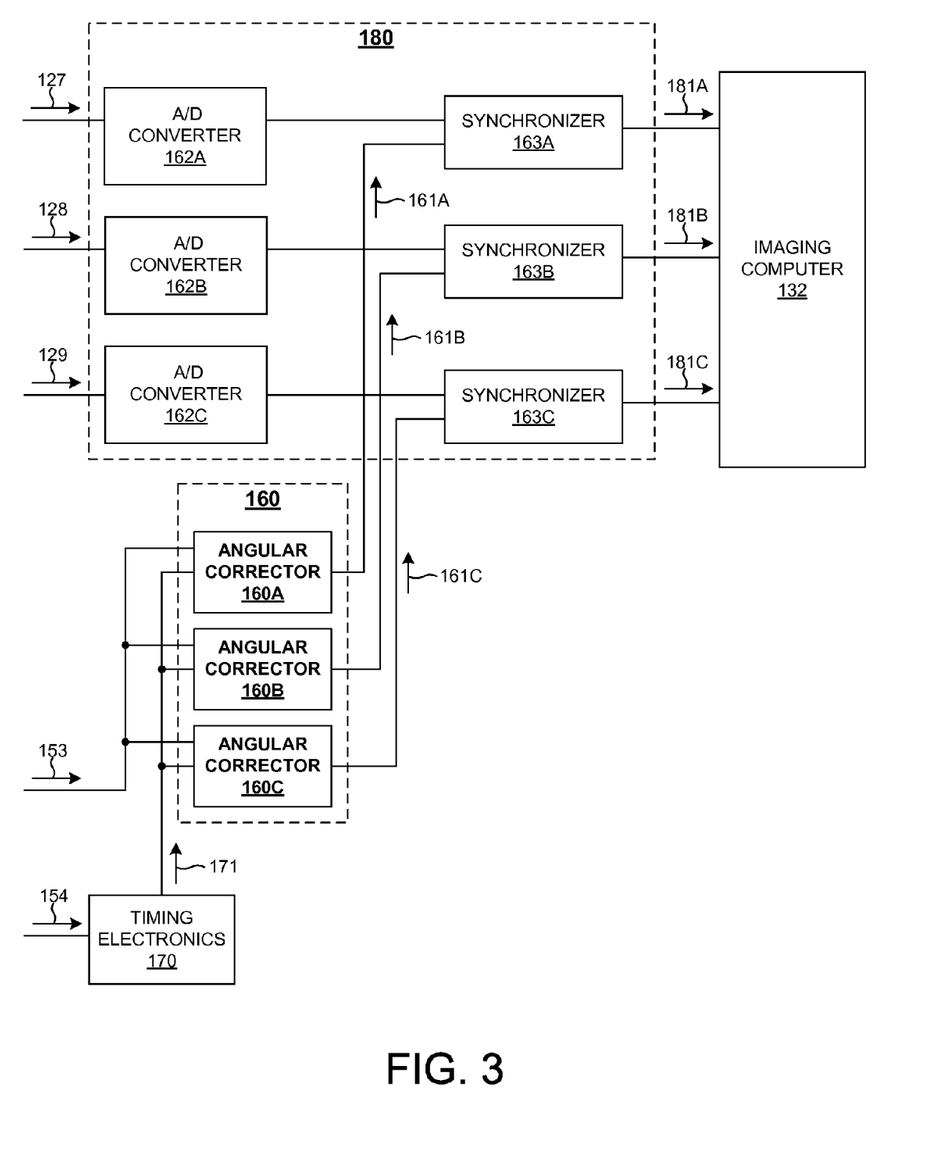
FIG. 3 is a diagram illustrative of angular corrector 160, timing electronics 170, and data acquisition electronics 180 of multi-spot inspection system 100 in greater detail.
Figure 5:
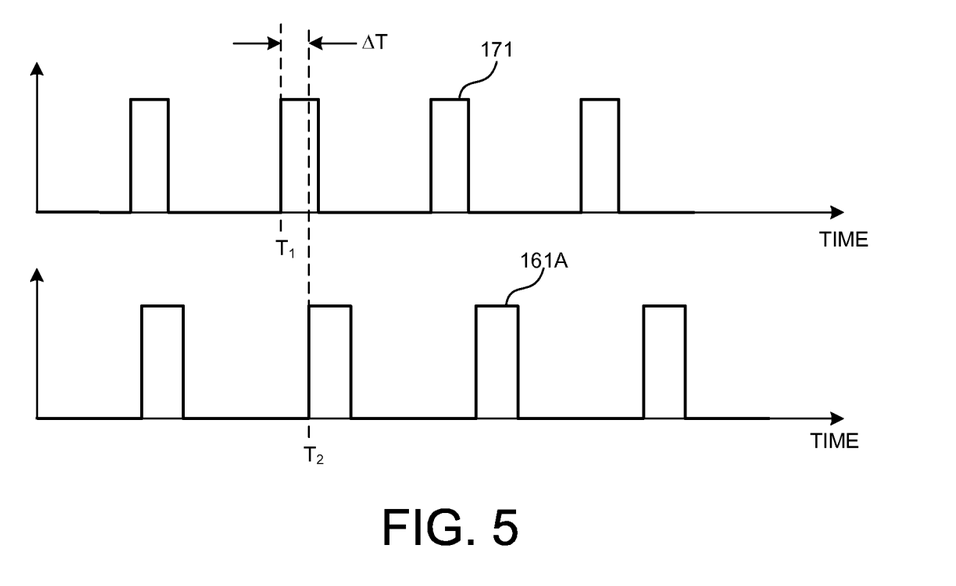
FIG. 5 illustrates an exemplary uncorrected data acquisition trigger signal 171 and an exemplary corrected data acquisition trigger signal 160A plotted as a function of time.

FIG. 3 is a diagram illustrative of angular corrector 160, timing electronics 170, and data acquisition electronics 180 in greater detail. As depicted, timing electronics 170 receives signal 154 indicative of encoder pulses generated by rotary encoder 151. Timing electronics 171 interpolates the encoder pulses and generates a signal 171 of high resolution pulses indicative of the angular position of wafer 123. FIG. 5 illustrates an exemplary signal 171 plotted as a function of time. As depicted, angular corrector 160A receives signal 171 and signal 153. Signal 153 is generated by linear encoder 152 and is indicative of the position of wafer 123 along the trajectory of the axis of rotation, T. Angular corrector 160A determines an angular correction value associated with incident spot 115A. The determination is made based on the misalignment distance associated with incident spot 115A, the radial distance between the axis of rotation of rotary stage 110 and the incident spot 115A at the current instance in time, and the radial distance between the axis of rotation of rotary stage 110 and the incident spot 115A at an instance in time when the wafer 123 was oriented at the same angular position. In one example, angular corrector 160A computes angular correction value, $\beta$, in accordance with Equation (5). As depicted in FIG. 2, R1 is the radial distance between the axis of rotation 150 of rotary stage 110 and the incident spot 115A at the current instance in time. R2 is the radial distance between the axis of rotation 150 of rotary stage 110 and the incident spot 115A when the wafer 123 was last oriented at angular position, $\gamma$. $A_O$ is the misalignment distance associated with incident spot 115A. The angular correction value, $\beta$, provides a spatial expression of the angular error induced by the misalignment of incident spot 115A with the trajectory of the axis of rotation, T. Angular corrector 160A then determines a time shift associated with the angular error. For an angular velocity, $\omega$, the desired time shift is $\beta/\omega$. Angular corrector 160 generates a corrected data acquisition trigger signal 161A where the corresponding pulse of signal 171 is shifted in time by a time $\Delta T=\beta/\omega$. FIG. 5 illustrates an exemplary corrected data acquisition trigger signal 160A where the current pulse is shifted in time by $\Delta T$. The corrected data acquisition trigger signal 161A is communicated to synchronizer 163A. Analog-to-digital converter 162A samples output 127 generated by detector 140. Synchronizer 163A subsamples data coming from analog-to-digital converter 162A with relatively low frequency trigger signal 161A and output data 181A is communicated to imaging computer 132.

A multi-spot system, such as multi-spot inspection system 100 includes multiple incident spots that each requires their own angular correction. In general, each corrected angular sample will have a different frequency and phase. FIG. 4 is a diagram illustrative of an array of incident spots 115 on wafer 123. By way of non-limiting example, multi-spot inspection system 100 is configured to inspect wafer 123 at three different incident spots 115A, 115B, and 115C. As depicted in FIG. 4, the misalignment distance between each incident spot and the trajectory of the axis of rotation, T, is different. Hence, data acquisition timing associated with each spot must be corrected by a different amount of time. Thus, angular corrector 160 includes angular correctors 160A, 160B, and 160C, each associated with incident spots 115A, 115B, and 115C, respectively. Angular corrector 160B generates a corrected data acquisition trigger signal 161B in a similar manner as described hereinbefore with reference to angular corrector 160A, except that misalignment distance, $A_O$, is replaced by misalignment distance, $B_O$, associated with incident spot 115B. The corrected data acquisition trigger signal 161B is communicated to synchronizer 163B. Analog-to-digital converter 162B samples output 128 generated by detector 120. Synchronizer 163B subsamples data coming from analog-to-digital converter 162B with relatively low frequency trigger signal 161B and output data 181B is communicated to imaging computer 132. Similarly, angular corrector 160C replaces $A_O$ with misalignment distance, $C_O$, associated with incident spot 115C to determine corrected data acquisition trigger signal 161C. The corrected data acquisition trigger signal 161C is communicated to synchronizer 163C. Analog-to-digital converter 162C samples output 129 generated by detector 130. Synchronizer 163C subsamples data coming from analog-to-digital converter 162C with relatively low frequency trigger signal 161C and output data 181C is communicated to imaging computer 132.

Each of the misalignment distances are determined apriori by a calibration routine designed to determine these distances based on measurements of known wafers.

In the embodiment of FIG. 1, the angular correction is manifested as a shifting in time of trigger points of the data acquisition system to allow the wafer to be located under the inspection location at the desired coordinate location. In some embodiments, the angular correction is recalculated and applied at each trigger point. This results in a slow shift in sampling frequency over the course of the surface scan.

In some other examples, the angular correction is applied as a post-processing step. In other words, in some embodiments, the data has already been collected based on uncorrected trigger points from timing electronics 170. However, the angular error can be removed from the resulting image by remapping the data collected to a corrected set of polar coordinates in the wafer coordinate frame. This can be achieved using the angular correction value, $\beta$, determined for each sample point. The data collected at each trigger point is spatially shifted based on angular correction value, $\beta$, to realize a corrected image. It should be noted that this is a computationally intensive process due to the quantity of data involved. Thus, it is preferable to correct for errors in angular position on the fly, rather than perform the operation as a post-processing step.

Figure 6:
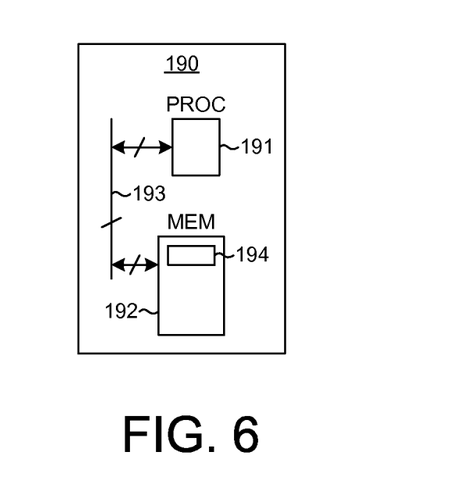
FIG. 6 is a diagram illustrative of a computer 190 configured to implement angular error correction functionality in accordance with the methods described herein.

A rotary inspection system such as multi-spot inspection system 100 includes a processor 191 and an amount of computer readable memory 192. Processor 191 and memory 192 may communicate over bus 193. Memory 192 includes an amount of memory 194 that stores a program code that, when executed by processor 191, causes processor 191 to determine an angular correction value based at least in part on a misalignment distance, a first radial distance between a center of rotation of a rotary stage and the first fixed inspection location at a first instance of an angular position, and a second radial distance between the center of rotation of the rotary stage and the first fixed inspection location at a second instance of the angular position.

In the embodiment depicted in FIG. 6, computer 190 includes processor 191 and memory 192 and implements angular error correction functionality in accordance with the methods described herein. Hence, in some embodiments, computer 190 is an angular corrector as described herein. However, in other embodiments, angular error correction functionality may be implemented by any other general purpose computer or dedicated hardware configured to operate in an analogous manner.

It should be recognized that the various elements described throughout the present disclosure may be carried out by a single computer system 190 or, alternatively, a multiple computer system 190. Moreover, different subsystems of the system 100, such as the motion controller 114, may include a computer system suitable for carrying out at least a portion of the elements described herein. Therefore, the aforementioned description should not be interpreted as a limitation on the present invention but merely an illustration. Further, the one or more computing systems 190 may be configured to perform any other element(s) of any of the method embodiments described herein.

In addition, the computer system 190 may be communicatively coupled to any of the timing electronics 170 and the data acquisition electronics 180 in any manner known in the art. In another example, the timing electronics 170, the angular corrector 160, and the data acquisition electronics 180 may be controlled by a single computer system.

The computer system 190 of the system 100 may be configured to receive and/or acquire data or information from the subsystems of the system (e.g., motion controller 114, linear encoder 152, rotary encoder 151, and the like) by a transmission medium that may include wireline and/or wireless portions. In this manner, the transmission medium may serve as a data link between the computer system 190 and other subsystems of the system 100. Further, the computing system 190 may be configured to receive data via a storage medium (i.e., memory). For instance, the misalignment distances associated with each incident spot may be stored in a permanent or semi-permanent memory device (not shown). In this regard, the misalignment distances may be imported from an external system.

Moreover, the computer system 190 may send data to external systems via a transmission medium. Moreover, the computer system 190 of the system 100 may be configured to receive and/or acquire data or information from other systems by a transmission medium that may include wireline and/or wireless portions. In this manner, the transmission medium may serve as a data link between the computer system 190 and other subsystems of the system 100. Moreover, the computer system 190 may send data to external systems via a transmission medium.

The computing system 190 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Figure 7:
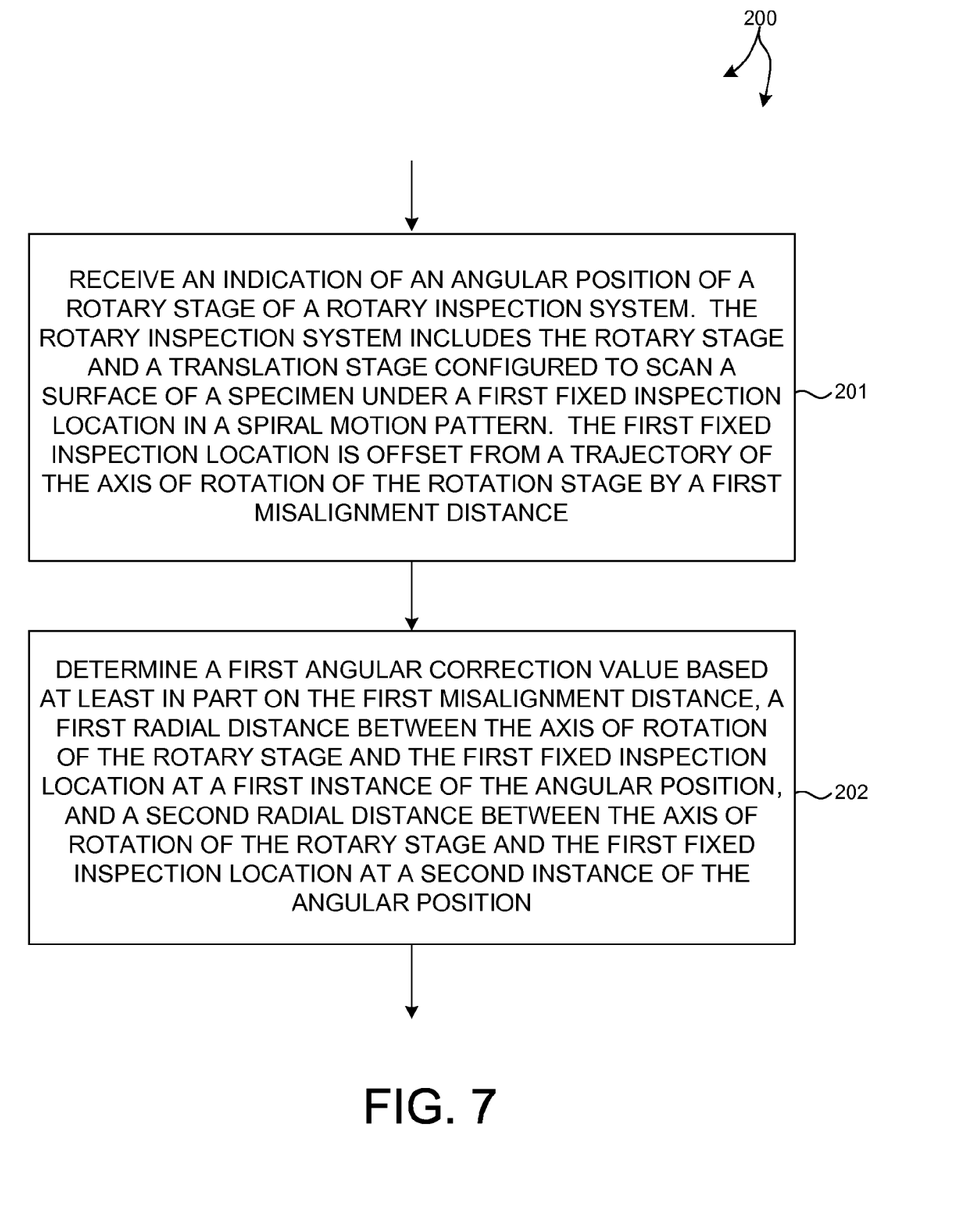
FIG. 7 is a flowchart illustrative of a method 200 for angular error correction.

FIG. 7 illustrates a method 200 for angular error correction suitable for implementation by a rotary inspection system such as the multi-spot inspection 100. In one aspect, it is recognized that data processing blocks of method 200 may be carried out via a pre-programmed algorithm executed by one or more processors of computing system 190. While the following description is presented in the context of inspection system 100, it is recognized herein that the particular structural aspects of inspection system 100 do not represent limitations and should be interpreted as illustrative only.

In block 201, angular corrector 160 receives an indication of an angular position of a rotary stage of a rotary inspection system. The rotary inspection system includes the rotary stage and a translational stage configured to scan a surface of a specimen under a first fixed inspection location in a spiral motion pattern. The first fixed inspection location is offset from a trajectory of the axis of rotation of the rotary stage by a first misalignment distance.

In block 202, angular corrector 160 determines a first angular correction value based at least in part on the first misalignment distance, a first radial distance between the axis of rotation of the rotary stage and the first fixed inspection location at a first instance of the angular position, and a second radial distance between the axis of rotation of the rotary stage and the first fixed inspection location at a second instance of the angular position.

Although correction of angular error has been described with reference to a multi-spot inspection system 100, the inventive aspects described herein apply to a single spot inspection system as well.

As described herein, the term "inspection system" includes any system employed at least in part to characterize a specimen in any aspect. However, such terms of art do not limit the scope of the term "inspection system" as described herein. In addition, inspection system 100 may be configured for measurement of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from angular correction.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, detectors arrays 120, 130, and 140 can be replaced by fiber arrays. In one example, multi-spot inspection system 100 may include more than one light source (not shown). The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, a multi-spot system may illuminate the wafer over more than one illumination area simultaneously. The multiple illumination areas may spatially overlap. The multiple illumination areas may be spatially distinct. In some embodiments, a multi-spot system may illuminate the wafer over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, multi-spot inspection system 100 may be a scanning spot system with one or more illumination areas that scan independently from any motion of wafer 123. In some embodiments an illumination area is made to scan in a repeated pattern along a scan line. The scan line may or may not align with the scan motion of wafer 123.

Accordingly, various modifications, adaptations, and combinations of various features of the described embodiments can be practiced without departing from the scope of the invention as set forth in the claims.

What is claimed is:

1. A method comprising:
rotating a wafer attached to a rotary stage about an axis of rotation of the rotary stage;
translating the axis of rotation of the rotary stage along a trajectory by a translation stage, wherein the rotary stage and the translation stage are configured to scan a surface of a specimen under a first fixed inspection location in a spiral motion pattern, wherein the first fixed inspection location is offset from the trajectory of the axis of rotation by a first misalignment distance;
generating a signal indicative of an angular position of the rotary stage;
generating a signal indicative of a position of the axis of rotation along the trajectory; and
determining a first angular correction value based at least in part on the first misalignment distance, a first radial distance between the axis of rotation of the rotary stage and the first fixed inspection location at a first instance of the angular position, and a second radial distance between the axis of rotation of the rotary stage and the first fixed inspection location at a second instance of the angular position.

2. The method of claim 1, wherein the first instance and the second instance are separated by an integer multiple of three hundred sixty degrees.

3. The method of claim 1, further comprising:
receiving an uncorrected data acquisition trigger signal based on the angular position;
determining a corrected data acquisition trigger signal based on the first angular correction value; and
transmitting the corrected data acquisition trigger signal to a data acquisition module of the rotary inspection system.

4. The method of claim 3, wherein the determining of the corrected data acquisition trigger signal is based on shifting the uncorrected data acquisition trigger signal in time based on the first angular correction value.

5. The method of claim 1, further comprising:
associating an amount of collected data with a corrected angular position, wherein the corrected angular position is the angular position offset by the first angular correction value.

6. The method of claim 1, further comprising:
determining the first misalignment distance based on a calibration of the rotary inspection system.

7. The method of claim 1, further comprising:
determining a second angular correction value based at least in part on a second misalignment distance between a second fixed inspection location and the trajectory of the axis of rotation, a third radial distance between the axis of rotation of the rotary stage and the second fixed inspection location at the first instance of the angular position, and a fourth radial distance between the axis of rotation of the rotary stage and the second fixed inspection location at the second instance of the angular position.

8. A rotary inspection system comprising:
a rotary stage configured to rotate a wafer attached to the rotary stage about an axis of rotation of the rotary stage;
a translation stage configured to translate the axis of rotation of the rotary stage along a trajectory, wherein the rotary stage and the translation stage are configured to scan a surface of a specimen under a first fixed inspection location in a spiral motion pattern, wherein the first fixed inspection location is offset from the trajectory of the axis of rotation by a first misalignment distance;

a rotary encoder configured to generate a signal indicative of an angular position of the rotary stage;

a translation encoder configured to generate a signal indicative of a position of the axis of rotation along the trajectory; and an angular corrector configured to determine a first angular correction value based at least in part on the first misalignment distance, a first radial distance between the axis of rotation and the first fixed inspection location at a first instance of an angular position, and a second radial distance between the axis of rotation and the first fixed inspection location at a second instance of the angular position.

9. The rotary inspection system of claim 8, wherein the angular corrector is further configured to determine a corrected data acquisition trigger signal based on the first angular correction value, and transmit the corrected data acquisition trigger signal to a data acquisition module of the rotary inspection system.

10. The rotary inspection system of claim 9, wherein the determining of the corrected data acquisition trigger signal is based on shifting an uncorrected data acquisition trigger signal in time based on the first angular correction value.

11. The rotary inspection system of claim 8, wherein the angular corrector is further configured to associate an amount of collected data with a corrected angular position, wherein the corrected angular position is the angular position offset by the first angular correction value.

12. The rotary inspection system of claim 8, wherein the first misalignment distance is based on a calibration of the rotary inspection system.

13. The rotary inspection system of claim 8, wherein the angular corrector is further configured to determine a second angular correction value based at least in part on a second misalignment distance between a second fixed inspection location and the trajectory of the axis of rotation, a third radial distance between the axis of rotation of the rotary stage and the second fixed inspection location at the first instance of the angular position, and a fourth radial distance between the axis of rotation of the rotary stage and the second fixed inspection location at the second instance of the angular position.

14. An apparatus comprising:
a rotary stage configured to rotate a wafer attached to the rotary stage about an axis of rotation of the rotary stage;
a translation stage configured to translate the axis of rotation of the rotary stage along a trajectory, wherein the rotary stage and the translation stage are configured to scan a surface of a specimen under a first fixed inspection location in a spiral motion pattern, wherein the first fixed inspection location is offset from the trajectory of the axis of rotation by a first misalignment distance;
a rotary encoder configured to generate a signal indicative of an angular position of the rotary stage;
a translation encoder configured to generate a signal indicative of a position of the axis of rotation along the trajectory;

a processor; and
a non-transitory, computer-readable medium storing instructions that, when executed by the processor, cause the processor to:
receive an indication of an angular position of the rotary stage; and
determine a first angular correction value based at least in part on the first misalignment distance, a first radial distance between the axis of rotation of the rotary stage and the first fixed inspection location at a first instance of the angular position, and a second radial distance between the axis of rotation of the rotary stage and the first fixed inspection location at a second instance of the angular position.

15. The apparatus of claim 14, wherein the first instance and the second instance are separated by an integer multiple of three hundred sixty degrees.

16. The apparatus of claim 14, wherein the instructions further comprise instructions that, when executed by the processor, cause the apparatus to:
receive an uncorrected data acquisition trigger signal based on the angular position;
determine a corrected data acquisition trigger signal based on the first angular correction value; and
transmit the corrected data acquisition trigger signal to a data acquisition module of the rotary inspection system.

17. The apparatus of claim 16, wherein the determining of the corrected data acquisition trigger signal is based on shifting the uncorrected data acquisition trigger signal in time based on the first angular correction value.

18. The apparatus of claim 14, wherein the instructions further comprise instructions that, when executed by the processor, cause the apparatus to:
associate an amount of collected data with a corrected angular position, wherein the corrected angular position is the angular position offset by the first angular correction value.

19. The apparatus of claim 14, wherein the instructions further comprise instructions that, when executed by the processor, cause the apparatus to:
determine the first misalignment distance based on a calibration of the rotary inspection system.

20. The apparatus of claim 14, wherein the instructions further comprise instructions that, when executed by the processor, cause the apparatus to:
determine a second angular correction value based at least in part on a second misalignment distance between a second fixed inspection location and the trajectory of the axis of rotation, a third radial distance between the axis of rotation of the rotary stage and the second fixed inspection location at the first instance of the angular position, and a fourth radial distance between the axis of rotation of the rotary stage and the second fixed inspection location at the second instance of the angular position.

21. The rotary inspection system of claim 8, wherein the first instance and the second instance are separated by an integer multiple of three hundred sixty degrees.

* * * * *